United States Patent
Liu et al.

(10) Patent No.: US 9,694,214 B2
(45) Date of Patent: Jul. 4, 2017

(54) PREPARATION OF SILICONE MICROEMULSIONS

(75) Inventors: Yihan Liu, Midland, MI (US); Andreas Stammer, Pont-A-Celles (BE)

(73) Assignee: DOW CORNING CORPORATION, Midland, MI (US)

( * ) Notice: Subject to any disclaimer, the term of this patent is extended or adjusted under 35 U.S.C. 154(b) by 208 days.

(21) Appl. No.: 12/988,071

(22) PCT Filed: Apr. 9, 2009

(86) PCT No.: PCT/US2009/002233
§ 371 (c)(1),
(2), (4) Date: Mar. 25, 2011

(87) PCT Pub. No.: WO2009/128883
PCT Pub. Date: Oct. 22, 2009

(65) Prior Publication Data
US 2011/0165206 A1    Jul. 7, 2011

Related U.S. Application Data

(60) Provisional application No. 61/045,414, filed on Apr. 16, 2008.

(51) Int. Cl.
*A61Q 19/00* (2006.01)
*A61K 8/06* (2006.01)
*A61K 8/892* (2006.01)
*B01F 17/54* (2006.01)
*C08J 3/03* (2006.01)
*C08L 83/04* (2006.01)
*C09D 183/04* (2006.01)
*C10M 155/02* (2006.01)
*C14C 9/00* (2006.01)
*C08G 77/16* (2006.01)
*C08G 77/18* (2006.01)
*C08G 77/20* (2006.01)
*C08G 77/00* (2006.01)

(52) U.S. Cl.
CPC ............ *A61Q 19/00* (2013.01); *A61K 8/062* (2013.01); *A61K 8/068* (2013.01); *A61K 8/892* (2013.01); *B01F 17/0071* (2013.01); *C08J 3/03* (2013.01); *C08L 83/04* (2013.01); *C09D 183/04* (2013.01); *C10M 155/02* (2013.01); *C14C 9/00* (2013.01); *C08G 77/16* (2013.01); *C08G 77/18* (2013.01); *C08G 77/20* (2013.01); *C08G 77/70* (2013.01); *C08J 2383/04* (2013.01); *C08J 2383/06* (2013.01); *C10M 2229/04* (2013.01); *C10N 2220/082* (2013.01); *C10N 2250/021* (2013.01)

(58) Field of Classification Search
CPC ........... C08L 83/04; C08L 8/062; C08L 8/068
See application file for complete search history.

(56) References Cited

U.S. PATENT DOCUMENTS

| | | |
|---|---|---|
| 3,419,593 A | 12/1968 | Wiling |
| 3,445,420 A | 5/1969 | Kookootsedes et al. |
| 3,715,334 A | 2/1973 | Karstedt |
| 3,814,730 A | 6/1974 | Karstedt |
| 3,839,388 A | 10/1974 | Nitzsche et al. |
| 3,923,705 A | 12/1975 | Smith |
| 3,989,667 A | 11/1976 | Lee et al. |
| 4,312,801 A | 1/1982 | Bodin et al. |
| 4,564,693 A | 1/1986 | Riederer |
| 4,620,878 A | 11/1986 | Gee |
| 4,701,490 A | 10/1987 | Burkhardt et al. |
| 4,733,677 A | 3/1988 | Gee et al. |
| 5,035,832 A | 7/1991 | Takamura et al. |
| 5,175,325 A | 12/1992 | Brown et al. |
| 5,300,286 A * | 4/1994 | Gee ............................ 424/78.03 |
| 5,403,909 A | 4/1995 | Rubinsztajn |
| 5,457,220 A | 10/1995 | Razzano |

(Continued)

FOREIGN PATENT DOCUMENTS

| | | |
|---|---|---|
| EP | 0215470 A2 | 3/1987 |
| EP | 0382365 A2 | 8/1990 |

(Continued)

OTHER PUBLICATIONS

English language abstract for EP 0215470 extracted from espacenet.com database Apr. 4, 2011, 15 pages.
English language translation and abstract for JP 2000-026726 extracted from PAJ database Apr. 4, 2011, 40 pages.
PCT International Search Report for PCT/US2009/002233 dated Aug. 6, 2009, 4 pages.
English language abstract not available for JP H08-325456; however, see English language equivalent U.S. Pat. No. 5,504,150. Original document extracted from the espacenet.com database on Jan. 20, 2014, 12 pages.
English language abstract and machine-assisted English translation for JP H11-222554 extracted from the PAJ database on Jan. 20, 2014, 36 pages.
English language abstract and machine-assisted English translation for JP 2005-187687 extracted from the PAJ database on Jan. 20, 2014, 52 pages.

(Continued)

*Primary Examiner* — Kyle Purdy
(74) *Attorney, Agent, or Firm* — Warner Norcross & Judd LLP

(57) ABSTRACT

A mechanical method of making an oil-in-water microemulsion containing (A) a polysiloxane and (B) an inert fluid selected from an inert siloxane fluid and an inert organic fluid, where the average emulsion particle size is between 1 and 140 nanometers, is disclosed. The process involves the following steps: i) preparing an oil phase comprising a polysiloxane containing mixture by the polymerization of silane or siloxane containing monomers and/or oligomers in the presence of an inert fluid, a suitable catalyst and optionally an end-blocking agent; and ii) where required quenching the polymerization process; wherein the inert fluid is substantially retained within the resulting polysiloxane containing mixture; iii) if required, mixing one or more surfactants into the oil phase; iv) adding water to the oil phase, followed by applying agitation or shear to the mixture to arrive at an oil-in-water microemulsion; v) optionally diluting the oil-in-water microemulsion by adding more water.

24 Claims, No Drawings

(56) References Cited

U.S. PATENT DOCUMENTS

| | | | |
|---|---|---|---|
| 5,504,150 | A | 4/1996 | Gilson et al. |
| 5,705,562 | A | 1/1998 | Hill |
| 5,759,530 | A * | 6/1998 | Riccio et al. ............. 424/70.12 |
| 5,817,714 | A | 10/1998 | Graiver et al. |
| 6,001,928 | A | 12/1999 | Harkness et al. |
| 6,054,548 | A | 4/2000 | Currie et al. |
| 6,258,891 | B1 | 7/2001 | Hoxmeier |
| 6,448,196 | B1 | 9/2002 | Eglin et al. |
| 6,475,974 | B1 | 11/2002 | Leboucher et al. |
| 6,737,444 | B1 | 5/2004 | Liu |
| 7,041,088 | B2 | 5/2006 | Nawrocki et al. |
| 7,238,768 | B2 | 7/2007 | Hupfield et al. |
| 8,012,544 | B2 | 9/2011 | Liu |
| 2005/0143282 | A1 | 6/2005 | Creutz et al. |
| 2010/0137454 | A1 | 6/2010 | Barmes et al. |

FOREIGN PATENT DOCUMENTS

| | | |
|---|---|---|
| EP | 0404027 A2 | 12/1990 |
| EP | 0755959 A2 | 1/1997 |
| EP | 0774482 A2 | 5/1997 |
| EP | 0842974 A1 | 5/1998 |
| EP | 1031344 A2 | 8/2000 |
| EP | 1221455 A1 | 7/2002 |
| EP | 1254192 B1 | 11/2002 |
| EP | 1427772 B1 | 6/2004 |
| GB | 895091 A | 5/1962 |
| GB | 918823 A | 2/1963 |
| GB | 2252975 A | 8/1992 |
| GB | 2288183 A | 10/1995 |
| JP | H08-325456 A | 12/1996 |
| JP | H11-222554 A | 8/1999 |
| JP | 2000-026726 A | 1/2000 |
| JP | 2005-187687 A | 7/2005 |
| JP | 2006-515383 A | 5/2006 |
| JP | 2007-508413 A | 4/2007 |
| JP | 2010-506035 A | 2/2010 |
| WO | WO 01-25389 A1 | 4/2001 |
| WO | WO 01-49774 A2 | 7/2001 |
| WO | WO 01-79330 A1 | 10/2001 |
| WO | WO 03-064500 A2 | 8/2003 |
| WO | WO 2004-065458 A1 | 8/2004 |
| WO | WO 2005/016998 A | 2/2005 |
| WO | WO 2006-106362 A1 | 10/2006 |
| WO | WO 2008-045427 A1 | 4/2008 |

OTHER PUBLICATIONS

English language abstract not available for JP 2006-515383; however, see English language equivalent U.S. Pat. No. 6,737,444. Original document extracted from the espacenet.com database on Jan. 20, 2014, 15 pages.

English language abstract not available for JP 2007-508413; however, see English language equivalent U.S. Pat. No. 8,012,544. Original document extracted from the espacenet.com database on Jan. 20, 2014, 13 pages.

English language abstract not available for JP 2010-506035; however, see English language equivalent US 2010/0137454. Original document extracted from the espacenet.com database on Jan. 20, 2014, 14 pages.

* cited by examiner

PREPARATION OF SILICONE MICROEMULSIONS

RELATED APPLICATIONS

This application claims priority to and all the advantages of International Patent Application No. PCT/US2009/002233, filed on Apr. 9, 2009, which claims priority to U.S. Provisional Patent Application No. 61/045,414, filed on Apr. 16, 2008.

This disclosure relates to the preparation of silicone in water microemulsions, and the resulting microemulsions made from said processes.

Silicone emulsions are well known in the art. Such silicone emulsions can be made by processes such as (i) mechanical emulsification, or by (ii) emulsion polymerization. However, for those silicone having a viscosity of >1000000 mPa·s at 25° C., (i.e. those of high molecular weight) the preparation of their emulsions are, for all practical purposes, limited to emulsion polymerization. In contrast, emulsions of silicones with a low viscosity and hence a low molecular weight can easily be obtained mechanically.

Emulsions may be categorized by the size of the polysiloxane particles and the appearance of the emulsion. Typically three categories of emulsions are recognized in the art. These are standard emulsions, fine emulsions and microemulsions. The term "emulsion" used alone herein encompasses the three individual types of silicone emulsions.

Standard emulsions are characterized by a large particle size (typically greater than 300 nanometers) and appear to the human eye to be opaque (impenetrable to light). Standard emulsions are most commonly identified as those having an intense white appearance. Fine emulsions are characterized by a smaller particle size, from 300 to 140 nanometers, and are identified as those compositions which visually vary from white with a bluish tint to very slightly translucent. Microemulsions are characterized as those having a particle size of less than 140 nanometers and visually vary from translucent to transparent. This is because the microemulsions contain structures smaller than the wavelength of visible light. Microemulsions are often preferred due to their translucent to transparent appearance as they can be used in applications requiring clarity. Microemulsions also have the advantage of being the most stable against creaming or sedimentation.

Emulsion polymerization typically entails combining a reactive silicone oligomer or silane monomer, surfactant, polymerization catalyst and water. The mixture is agitated and the silicone oligomers or the silane monomers are allowed to polymerize until a standard emulsion, fine emulsion or microemulsion is formed. Typically alkoxysilanes or cyclic siloxanes are used as the reactive monomers and oligomers. Combinations of the silicone reactants can also be used to form copolymers in the resulting emulsion.

Mechanical emulsification usually entails taking the polysiloxane and using mechanical means such as homogenizers or vigorous agitation to emulsify the siloxanes in water. Typically a surfactant is added to the polysiloxane or water to aid the emulsification process. Mechanical emulsification employs two general methods: direct emulsification and emulsification by inversion. In the direct emulsification process, the oil phase is added to the aqueous phase under agitation to form a coarse emulsion, and the coarse emulsion is then subjected to high shear in a homogenizing device to reduce particle size. The direct mechanical method is suitable for oil phases of relatively low viscosity ($<10^3$-$10^4$ mPa·s at 25° C.) in order to reduce the particle size enough for the emulsion to be stable. Standard emulsions (particle size greater than 0.3 micrometer) are typically produced. Rarely can fine emulsions or microemulsions be made by the direct mechanical emulsification, particularly when the starting polymers have high viscosities e.g. $>10^4$ mPa·s at 25° C. and especially those having viscosities of $10^6$ mPa·s at 25° C. This is at least partially due to the energy required to mix such polymers, difficulties in introducing additional ingredients into the mixture (e.g. surfactants) and the resulting particle sizes required in order for e.g. a microemulsion to be formed.

Mechanical emulsification by inversion involves the phenomenon of phase inversion where the continuous phase of a starting emulsion becomes the dispersed phase in the final emulsion and vice versa. Phase inversion is triggered by either a change in surfactant affinity or a change in composition such as water-to-oil ratio. Therefore, for example, to make an oil-in-water emulsion by the inversion method, water can be added to the oil phase under agitation to induce a phase inversion resulting in an oil-in-water emulsion final product. This latter method generally requires the oil phase viscosity to be limited to less than 100,000 mPa·s at 25° C. for easy practical process handling, unless special devices such as a high pressure extruder is used. Further, microemulsions of small particle sizes can only be made with oil phase viscosities of less than 10,000 mPa·s at 25° C. in general.

The preparation of silicone microemulsions have been described in, for example EP1031344, EP1427772, EP1221455, U.S. Pat. Nos. ,6475,974, 4,620,878 and EP0755959. In U.S. Pat. No. 7,238,768 there is provided a method of preparing an amino functional polysiloxane comprises reacting an aminosilane (A) which contains an aminoalkyl group and at least one alkoxy group bonded to Si with a carboxylic acid and a silanol-functional polysiloxane (B), the amount of carboxylic acid (C) being such that the molar ratio of carboxylic acid groups of (C) to amino groups of aminosilane (A) is less than 1:1 and the amount of silanol-functional polysiloxane (B) being such that the molar ratio of silanol groups of (B) to Si-bonded alkoxy groups of aminosilane (A) is greater than 1:1, whereby the aminosilane (A) is at least partially converted into its carboxylate salt which acts as a catalyst for the siloxane condensation polymerization reaction between (A) and (B).

Because of the high viscosity of some silicones such as silicone gums and elastomers, their emulsion preparation has for all practical purposes been limited to emulsion polymerization. High molecular weight silicone microemulsions are in particular restricted to using the method of emulsion polymerization. However, emulsion polymerization is restricted to certain type of polymers that can be made, to requirement of certain level of monomer solubility in water, and to the limited classes of surfactant that can be employed. In contrast, silicones with a low viscosity and hence a low molecular weight can easily be obtained by mechanical emulsification, employing a variety of emulsifiers.

One way of overcoming this difficulty in emulsification is to dilute the high molecular weight silicone in a low viscosity fluid carrier. In addition, polymerization of the high molecular weight silicone in the presence of an inert non-reacting fluid in itself possesses advantages in terms of ease of handling and molecular weight control.

The applicant's co-pending application, WO 2008045427, which was published after the priority date of this application, describes the preparation of silicone oil-in-water emulsions having a polysiloxane containing polymer.

The process comprises preparing a polysiloxane containing polymer by the polymerisation of siloxane containing monomers and/or oligomers in the presence of an inert organopolysiloxane and/or an organic fluid, a suitable catalyst and optionally an end-blocking agent. If required, one or more surfactants may be introduced into the polysiloxane containing polymer to form a homogenous oil phase; adding water to the homogenous oil phase to form a water-in-oil emulsion, applying shear to the water-in-oil emulsion to cause inversion of the water-in-oil emulsion to an oil-in-water emulsion; and optionally diluting the oil-in-water emulsion by adding more water.

In accordance with the present disclosure there is provided a mechanical method of making an oil-in-water microemulsion containing (A) a polysiloxane and (B) an inert fluid selected from an inert siloxane fluid and an inert organic fluid where the average emulsion particle size is between 1 and 140 nanometers, comprising the steps of:
i) preparing an oil phase comprising a polysiloxane containing mixture by the polymerisation of silane or siloxane containing monomers and/or oligomers in the presence of an inert fluid, a suitable catalyst and optionally an end-blocking agent; and
ii) where required quenching the polymerisation process; wherein the inert fluid is substantially retained within the resulting polysiloxane containing mixture;
iii) if required, mixing one or more surfactants into the oil phase;
iv) adding water to the oil phase, followed by applying agitation or shear to the mixture to arrive at an oil-in-water microemulsion;
v) optionally diluting the oil-in-water microemulsion by adding more water.

The concept of "comprising" where used herein is used in its widest sense to mean and to encompass the notions of "include" and "consist of". All viscosity measurements referred to herein were measured at 25° C. unless otherwise indicated.

For purposes of our disclosure, a microemulsion contains structures having an average diameter of less than 140 nanometers, alternatively less than 100 nanometers.

For the sake of this application an inert fluid is a substantially non-volatile fluid which is intended to be unreactive towards any other constituent i.e. it does not chemically participate in the polymerisation reaction of step (i) or chemically interact with the additives introduced in any of steps (i) through to (vi). The inert fluid is not removed prior to emulsification. Hence the inert fluid is substantially present in the microemulsion.

The present disclosure provides an inexpensive technique for producing stable microemulsions from mixtures comprising silicone polymers having a wide viscosity spectrum in combination with one or more inert fluids selected from organopolysiloxane and/or an organic fluid. The inert fluid according to the present invention is typically a non-volatile but low viscosity fluid. One particular advantage is that it can be utilised to prepare microemulsions from such mixtures containing silicone polymers (which if traditionally prepared would have very high viscosities e.g. >1000000 mPa·s at 25° C. because of their high molecular weight) but when polymerised in the presence of the inert fluids the overall viscosity of the resulting mixture is significantly lower and therefore it is much easier to introduce surfactants and the like (if required) into the mixture prior to emulsification than it would be if no inert fluid was present. This was a surprising result as it is extremely difficult, if not impossible, to produce microemulsions from the majority, if not all, of these inert fluids on their own. It was therefore expected that the introduction of such inert fluids would hinder the formation of microemulsions when introduced into compositions of the present disclosure. But surprisingly the inventors have found that contrary to their expectations the inert fluids did not have a negative effect on the preparation of these microemulsions and the present invention provides an unexpectedly straight forward method to make stable microemulsions of these combinations mechanically and what is more the resultant microemulsions remain stable over time.

A polysiloxane containing polymer is intended to mean a polymer comprising multiple organosiloxane or polyorganosiloxane groups per molecule and is intended to include a polymer substantially containing only organosiloxane or polyorganosiloxane groups in the polymer chain and polymers where the backbone contains both organosiloxane and/or organic polymeric groups in the polymeric chain. Such polymers can be homopolymers or co-polymers, including, but not limited to, block co-polymers and random co-polymers.

In accordance with the present invention a polysiloxane polymer is polymerised in the presence of an inert fluid and may have the general formula:

$$R_{(3-a)}R^1_a SiO[(R_2SiO)_b]SiR_{(3-a)}R^1_a \qquad (1)$$

wherein each R is the same or different and is an alkyl group, a substituted alkyl group or an optionally substituted phenyl group; $R^1$ is hydrogen, a hydroxy group, a hydrolysable group or an unsaturated organic group; a is zero or 1, b is an integer of at least 200 alternatively at least 500, or alternatively at least 1500. The polysiloxane polymer according to the present invention may also comprise a degree of branching, therefore containing in addition units of the $RSiO_{3/2}$ structure and/or units of $SiO_{4/2}$, up to a level so long as the branching does not lead to macroscopic phase separation of the siloxane polymer and the inert fluid prior to emulsification.

For the purpose of this application "Substituted", when used in relation to hydrocarbon groups, means one or more hydrogen atoms in the hydrocarbon group has been replaced with another substituent. Examples of such substituents include, but are not limited to, halogen atoms such as chlorine, fluorine, bromine, and iodine; halogen atom containing groups such as chloromethyl, perfluorobutyl, trifluoroethyl, and nonafluorohexyl; oxygen atoms; oxygen atom containing groups such as (meth)acrylic and carboxyl; nitrogen atoms; nitrogen atom containing groups such as amines, amino-functional groups, amido-functional groups, and cyano-functional groups; sulphur atoms; and sulphur atom containing groups such as mercapto groups, and polyoxyethylene and polyoxypropylene groups.

When R is an alkyl group it may comprise any suitable alkyl group such as methyl, ethyl, propyl, butyl, amyl, hexyl, octyl, decyl, dodecyl, octadecyl, and myricyl groups. R may also comprise cycloalkyl groups such as cyclobutyl and cyclohexyl groups; aryl groups such as the phenyl, xenyl and naphthyl groups; aralkyl groups such as the benzyl and 2-phenylethyl groups; alkaryl groups such as the tolyl, xylyl and mesityl groups.

Alternatively the substituted alkyl groups, when present, in accordance with the present disclosure, may contain at least one polar group attached to silicon through a silicon-carbon bond or a silicon-oxygen-carbon bond. Suitable polar groups may contain substituents such as amines, amine salts, amides, carbinols, carboxylic acids, carboxylic acid salts, phenols, sulfonate salts, sulfate salts, phosphate acids, and phosphate acid salts, where the polar group is attached to silicon through silicon-carbon or silicon-oxygen-carbon bonds or the polar groups may be hydroxyl groups. It is preferred that R be a hydrocarbon group containing from 1 to 18 carbon atoms.

When the polar group is an amine this may be selected from unsubstituted amine group —$NH_2$, alkyl substituted amine groups such as —$NH(CH_2)_{n'}CH_3$ where n' is zero or an integer from 1 to 6, and —$N((CH_2)_{n'}CH_3)_2$; where n' is as above and aminoalkyl substituted amine groups such as —$NH(CH_2)_{n''}NH_2$ where n" is an integer from 1 to 6, —$NH(CH_2)_6NH_2$, and —$NH(CH_2)_{n''}N(CH_3)_2$. Salts of these same amine-functional groups may also be used in the present disclosure. Examples of such salts include alkyl carboxylate salts, aryl carboxylate salts, halide salts such as chlorides and bromides, and other neutralization products of amines with organic acids.

When present the amine functional polysiloxane component of the present disclosure is a silicone fluid with highly polar pendant aminoalkyl modifying groups.

Particularly preferred amine functional polysiloxanes include reactive and non-reactive hydrolysable and non-hydrolysable derivatives which are wholly, or in part, terminally substituted with aminopropyl, aminobutyl, or diamino pendant chains.

In accordance with one embodiment of the disclosure the amine functional polysiloxane employed has the formula:

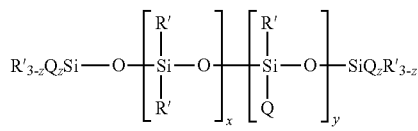

wherein R' denotes an alkyl group of 1 to 4 carbons or a phenyl group with the proviso that at least 50 percent of the total number of R' groups are methyl; Q denotes an amine functional substituent of the formula —R"Z wherein R" is a divalent alkylene group of 3 to 6 carbon atoms and Z is a monovalent group selected from the group consisting of —$NR_2'''$, and —$NR'''(CH_2)_bNR_2'''$; wherein R''' denotes hydrogen or an alkyl group of 1 to 4 carbons, and b is a positive integer having a value of from 2 to 6; z has a value of 0 or 1; x has an average value of 25 to 3000; y has an average value of 0 to 100 when z is 1, y has an average value of 1 to 100 when z is 0; with the proviso that in all cases y has an average value that is not greater than one tenth the average value of x. This embodiment might, for example, utilize an amine functional polysiloxane resulting from the polymerisation of a linear hydroxyl terminated siloxane oligomer with an amine functional dialkoxysilane.

Alternatively, amine functional polysiloxane result from the polymerization of siloxane or silane containing monomers and/or oligomers in the presence of an inert fluid according to the present disclosure is a branched silicone fluid with polar pendant aminoalkyl modifying groups. Such a branched amine functional silicone can be a reaction product of reactive siloxanes and/or silanes containing $SiO_{3/2}$ unit. One example, but not here to limit the scope of the disclosure, would be the polymerization of a linear hydroxyl terminated siloxane oligomer with an amine functional trialkoxysilane.

Another suitable polysiloxane resulted from polymerization of siloxane or silane containing monomers and/or oligomers in the presence of an inert fluid according to the present disclosure is a polysiloxane containing at least one group having a quaternary ammonium group. This can be obtained by polymerization of siloxanes or silanes involving at least one reactant having the ammonium functional group. Alternatively, the quaternary ammonium functional group in the polysiloxane can be obtained by quaternizing the amine functional group of an amine polysiloxane resulted from polymerization of siloxane or silane containing monomers and/or oligomers in the presence of an inert fluid.

When present the amount of amine or quaternary ammonium group is alternatively from that 1 to 20, alternatively 2 to 10 molar percent of the number of silicon atoms in the polysiloxane is linked to the group containing the amine or quaternary ammonium group.

Two types of amide-functional polar groups may be illustrated by the general formulae

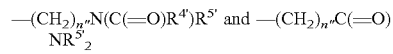

where n" is as hereinbefore described, $R^{4'}$ is a monovalent alkyl group containing from 1 to 6 carbon atoms, and $R^{5'}$ is selected from the group consisting of hydrogen, alkyl groups containing from 1 to 4 carbon atoms, and

The polar group on the polyorganosiloxane may also be in the form of a carbinol. In general, examples of suitable carbinol groups may be represented by the general formula

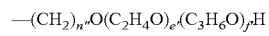

where n" is as hereinbefore described and e' and f' are both greater than or equal to zero. When both e' and f' equal zero the carbinol groups are simple alcohol groups. When e' is greater than zero the carbinol contains an ethylene glycol portion; where f' is greater than zero the carbinol contains a propylene glycol portion.

Other suitable polar groups or substituents include carboxylic acids and their salts. These polar groups may contain one or more COOH groups or their salts Examples of the cations capable of forming carboxylic acid salts suitable for use in this disclosure include $Na^+$, $K^+$, $Li^+$, $NH_4^+$, and pyridinium ions.

The polar group may also be of the phenol type expressed by the general formula

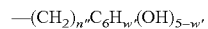

where n" is as hereinbefore described and where w' is 0 to 4.

Other polar groups or substituents suitable for incorporation in the polyorganosiloxanes of this disclosure include the sulphonic acid salts and sulfate salts. Examples of such polar groups are illustrated by the general formula

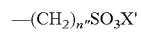

for the sulphonic acid salt and

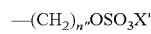

for the sulfate salt where X' is a suitable cation such as $Na^+$, $K^+$, $Li^+$ and $NH_4^+$.

The polar groups may also be in the form of phosphate acids and phosphate acid salts of the general formula

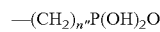

or

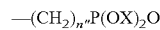

respectively, where n" and X' are as hereinbefore described.

Whilst preferably the polysiloxane containing polymer has a substantially organopolysiloxane molecular chain, the polysiloxane containing polymer may alternatively contain a block copolymeric backbone comprising at least one block of siloxane groups and an organic component comprising any suitable organic based polymer backbone for example the organic polymer backbone may comprise, for example, polystyrene and/or substituted polystyrenes such as poly(α-methylstyrene), poly(vinylmethylstyrene), dienes, poly(p-trimethylsilylstyrene) and poly(p-trimethylsilyl-α-methylstyrene). Other organic components which may be incorporated in the polymeric backbone may include acetylene terminated oligophenylenes, vinylbenzyl terminated aromatic polysulphones oligomers, aromatic polyesters, aromatic polyester based monomers, polyalkylenes, polyurethanes, aliphatic polyesters, aliphatic polyamides and aromatic polyamides and the like.

However perhaps the most preferred organic based polymeric blocks in polysiloxane containing polymer are polyoxyalkylene based blocks. The oxyalkylene units are not necessarily identical throughout the polyoxyalkylene monomer, but can differ from unit to unit. A polyoxyalkylene block, for example, can be comprised of oxyethylene units, ($-C_2H_4-O-$); oxypropylene units ($-C_3H_6-O-$); or oxybutylene units, ($-C_4H_8-O-$); or mixtures thereof. Alternatively the polyoxyalkylene polymeric backbone consists essentially of oxyethylene units and/or oxypropylene units.

Other polyoxyalkylene blocks in the polysiloxane containing polymer may include for example units of the structure—

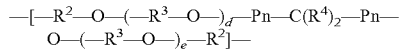

in which Pn is a 1,4-phenylene group, each $R^2$ is the same or different and is a divalent hydrocarbon group having 2 to 8 carbon atoms, each $R^3$ is the same or different and, is, an ethylene group propylene group or isopropylene group, each $R^4$ is the same or different and is a hydrogen atom or methyl group and each of the subscripts d and e is a positive integer in the range from 3 to 30.

In another embodiment, the polysiloxane polymer prepared according to the present invention contains" a low content of volatile siloxanes with a boiling point below 250° C. This can be achieved by evaporation or extracting the volatile species from the polysiloxane polymer or by using polymerization conditions that result in low volatility content. Such conditions can be, but are not limited to polymerization at low temperature, or use of catalysts that favour condensation reactions rather than equilibration.

The inert fluid is in accordance with the present invention selected from an inert siloxane fluid and an inert organic fluid. The inert fluid may be selected from an organopolysiloxane extender and/or plasticiser and/or an organic extender or plasticiser or a cyclic siloxane comprising between 3 and 20 silicon atoms. Preferably the inert fluid has a viscosity of from 0.65 mPa·s at 25° C.-10000 mPa·s at 25° C.

Reference herein to the terms "extender" and/or "plasticiser" are referring to additives, commonly used in silicone based compositions as e.g. room temperature cure sealants, which serve to "extend" and/or "plasticize" the silicone sealant composition by blending. Plasticisers and extenders (sometimes also referred to as a process aid or secondary plasticiser) are used to dilute the sealant composition and basically make the sealant more economically competitive without substantially negatively affecting the properties of the sealant formulation. Typically in the case of the introduction of plasticisers, properties of the sealant formulation may be enhanced.

Suitable inert liquids include trialkylsilyl terminated polydialkylsiloxanes and derivatives thereof which may comprise a degree of substitution, with the provision that any substituted groups in the inert fluid do not participate in the polymerisation reaction. The substituted groups on the inert fluid are alternatively the same as those identified in the previous definition of substituted groups with respect to hydrocarbon groups. Alternatively each alkyl group may be the same or different and comprises from 1 to 8 carbon atoms, alternatively is a methyl or ethyl group, alternatively with a viscosity of from 0.65 to 100 000 mPa·s at 25° C., or alternatively from 10 to 1000 mPa·s at 25° C.

The inert fluid may comprise any suitable organic extender/organic plasticiser. Mineral oil extenders and plasticisers are however particularly preferred.

Examples include linear or branched mono unsaturated hydrocarbons such as linear or branched alkenes or mixtures thereof containing at least 12, e.g. from 12 to 25 carbon atoms; and/or mineral oil fractions comprising linear (e.g. n-paraffinic) mineral oils, branched (iso-paraffinic) mineral oils, cyclic (referred in some prior art as naphthenic) mineral oils and mixtures thereof. Alternatively the hydrocarbons utilised comprise at least 10, alternatively at least 12 or alternatively greater than 20 carbon atoms per molecule.

Alternative mineral oil extenders include alkylcycloaliphatic compounds, low molecular weight polyisobutylenes, phosphate esters, alkybenzenes including polyalkylbenzenes which are unreactive with the polymer. An alternative class of extenders are esters of mono, di and polycarboylic acids.

Any suitable mixture of mineral oil fractions may be utilised as the inert fluid in the present disclosure but high molecular weight extenders (e.g. >220 g/mol) are particularly preferred. Examples include: alkylcyclohexanes (molecular weight >220 g/mol); paraffinic hydrocarbons and mixtures thereof containing from 1 to 99%, alternatively from 15 to 80% n-paraffinic and/or isoparaffinic hydrocarbons (linear branched paraffinic) and 1 to 99%, alternatively 85 to 20% cyclic hydrocarbons (naphthenic) and a maximum of 3%, alternatively a maximum of 1% aromatic carbon atoms. The cyclic paraffinic hydrocarbons (naphthenics) may contain cyclic and/or polycyclic hydrocarbons. Any suitable mixture of mineral oil fractions may be used, e.g. mixtures containing (i) 60 to 80% paraffinic and 20 to 40% naphthenic and a maximum of 1% aromatic carbon atoms;
(ii) 30-50%, alternatively 35 to 45% naphthenic and 70 to 50% paraffinic and or isoparaffinic oils;
(iii) hydrocarbon fluids containing more than 60 wt. % naphthenics, at least 20 wt. % polycyclic naphthenics and an ASTM D-86 boiling point of greater than 235° C.;
(iv) hydrocarbon fluid having greater than 40 parts by weight naphthenic hydrocarbons and less than 60 parts by weight paraffinic and/or isoparaffinic hydrocarbons based on 100 parts by weight of hydrocarbons.

Alternatively the mineral oil based extender or mixture thereof comprises at least one of the following parameters:
(i) a molecular weight of greater than 150 g/mol, alternatively greater than 200;
(ii) an initial boiling point equal to or greater than 230° C. (according to ASTM D 86).
(iii) a viscosity density constant value of less than or equal to 0.9; (according to ASTM 2501)
(iv) an average of at least 12 carbon atoms per molecule, alternatively 12 to 30 carbon atoms per molecule;

(v) an aniline point equal to or greater than 70° C., alternatively the aniline point is from 80 to 110° C. (according to ASTM D 611);
(vi) a naphthenic content of from 20 to 70% by weight of the extender and a mineral oil based extender has a paraffinic content of from 30 to 80% by weight of the extender according to ASTM D 3238);
(vii) a pour point of from −50 to 60° C. (according to ASTM D 97);
(viii) a kinematic viscosity of from 1 to 20 cSt at 40° C. (according to ASTM D 445)
(ix) a specific gravity of from 0.7 to 1.1 (according to ASTM D1298);
(x) a refractive index of from 1.1 to 1.8.at 20° C. (according to ASTM D 1218)
(xi) a density at 15° C. of greater than 700 kg/m$^3$ (according to ASTM D4052) and/or
(xii) a flash point of greater than 100° C., alternatively greater than 110° C. (according to ASTM D 93)
(xiii) a saybolt colour of at least +30 (according to ASTM D 156)
(xiv) a water content of less than or equal to 250 ppm
(xv) a Sulphur content of less than 2.5 ppm (according to ASTM D 4927)

Other organic extenders may include for the sake of example, fatty acids and fatty acid esters, alkylbenzene compounds suitable for use include heavy alkylate alkylbenzene or an alkylcycloaliphatic compound. Examples of alkyl substituted aryl compounds useful as extenders and/or plasticisers are compounds which have aryl groups, especially benzene substituted by alkyl and possibly other substituents, and a molecular weight of at least 200.

The alkylbenzene compounds suitable for use include heavy alkylate alkylbenzene or an alkylcycloaliphatic compound. Examples of alkyl substituted aryl compounds useful as extenders and/or plasticisers are compounds which have aryl groups, especially benzene substituted by alkyl and possibly other substituents, and a molecular weight of at least 200. Examples of such extenders are described in U.S. Pat. No. 4,312,801, the content of which is incorporated herein by reference. These compounds can be represented by general formula (2), (3), (4) and (5):

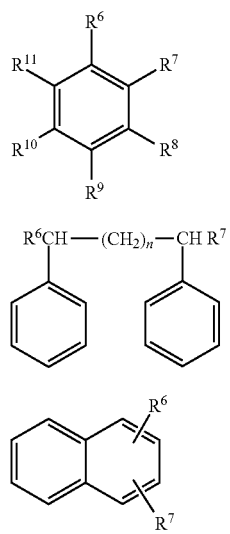

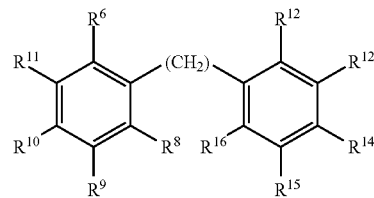

where $R^6$ is an alkyl chain of from 1 to 30 carbon atoms, each of $R^7$ through to $R^{16}$ is independently selected from hydrogen, alkyl, alkenyl, alkynyl, halogen, haloalkyl, nitrile, amine, amide, an ether such as an alkyl ether or an ester such as an alkyl ester group, and n is an integer of from 1 to 25.

Of these formula (2) where each of $R^7$, $R^8$, $R^9$, $R^{10}$ and $R^{11}$ is hydrogen and $R^6$ is a $C_{10}$-$C_{13}$ alkyl group. A particularly useful source of such compounds are the so-called "heavy alkylates", which are recoverable from oil refineries after oil distillation. Generally distillation takes place at temperatures in the range of from 230 to 330° C., and the heavy alkylates are present in the fraction remaining after the lighter fractions have been distilled off.

Examples of alkylcycloaliphatic compounds are substituted cyclohexanes with a molecular weight in excess of 220. Examples of such compounds are described in EP 0842974, the content of which is incorporated herein by reference. Such compounds may be represented by general formula (6).

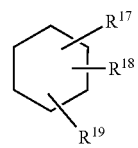

where $R^{17}$ is a straight or branched alkyl group of from 1 to 25 carbon atoms, and $R^{18}$ and $R^{19}$ are independently selected from hydrogen or a $C_{1-25}$ straight or branched chain alkyl group.

Alternatively the inert fluid may comprise may comprise a suitable non-mineral based natural oil or a mixture thereof, i.e. those derived from animals, seeds and nuts and not from mineral oils (i.e. not from petroleum or petroleum based oils) such as for example almond oil, avocado oil, beef tallow, borrage oil, butterfat, canola oil, cardanol, cashew nut oil, cashew nutshell liquid, castor oil, citrus seed oil, cocoa butter, coconut oil, cod liver oil, corn oil, cottonseed oil, cuphea oil, evening primrose oil, hemp oil, jojoba oil, lard, linseed oil, macadamia oil, menhaden oil, oat oil, olive oil , palm kernel oil, palm oil peanut oil, poppy seed oil, rapeseed oil, rice bran oil, safflower oil, safflower oil (high oleic), sesame oil, soybean oil, sunflower oil, sunflower oil (high oleic), tall oil, tea tree oil, turkey red oil, walnut oil perilla oil, dehydrated castor oils, apricot oil, pine nut oil, kukui nut oil, amazon nut oil almond oil, babasu oil, argan oil, black cumin oil, bearberry oil, calophyllum oil, camelina oil, carrot oil, carthamus oil, cucurbita oil, daisy oil, grape seed oil, foraha oil, jojoba oil, queensland oil, onoethera oil, ricinus oil, tamanu oil, tucuma oil, fish oils such as pilchard, sardine and herring oils. The extender may alternatively comprise mixtures of the above and/or derivatives of one or more of the above.

A wide variety of natural oil derivates are available. These include transesterified natural vegetable oils, boiled natural oils such as boiled linseed oil, blown natural oils and stand natural oils. An example of a suitable transesterified natural vegetable oil is known as biodiesel oil, the transesterification product produced by reacting mechanically extracted natural vegetable oils from seeds, such as rape, with methanol in the presence of a sodium hydroxide or potassium hydroxide catalyst to produce a range of esters dependent on the feed utilised. Examples might include for example methyloleate $(CH_3(CH_2)_7CH=CH(CH_2)_7CO_2CH_3)$.

Stand natural oils which are also known as thermally polymerised or heat polymerised oils and are produced at elevated temperatures in the absence of air. The oil polymerises by cross-linking across the double bonds which are naturally present in the oil. The bonds are of the carbon-carbon type. Stand oils are pale coloured and low in acidity. They can be produced with a wider range of viscosities than blown oils and are more stable in viscosity. In general, stand oils are produced from linseed oil and soya bean oil but can also be manufactured based on other oils. Stand oils are widely used in the surface coatings industry.

Blown oils which are also known as oxidised, thickened and oxidatively polymerised oils and are produced at elevated temperatures by blowing air through the oil. Again the oil polymerises by cross-linking across the double bonds but in this case there are oxygen molecules incorporated into the cross-linking bond. Peroxide, hydroperoxide and hydroxyl groups are also present. Blown oils may be produced from a wider range of oils than stand oils. In general, blown oils are darker in colour and have a higher acidity when compared to stand oils. Because of the wide range of raw materials used, blown oils find uses in many diverse industries, for example blown linseed oils are used in the surface coatings industry and blown rapeseed oils are often used in lubricants.

The amount of inert fluid which may be included in the composition will depend upon factors such as the purpose to which the composition is to be put, the molecular weight of the inert fluid(s) concerned etc. In general however, the higher the molecular weight of the inert fluids(s), the less will be tolerated in the composition but such high molecular weight inert fluids have the added advantage of lower volatility. Typical compositions will contain up to 70% inert fluids(s), or alternatively up to 50%. More suitable polymer products comprise from 5-60% w/w of inert fluid(s).

Such polysiloxane containing polymers as prepared in step (i) of the process in accordance with the present disclosure may be made by a variety of routes with the polymers produced being end-capped with compounds which will provide the required terminal groupings on the polymer and provided the polymer or its precursors and/or intermediates is/are diluted in the inert fluid described above during the polymerisation process. Preferred routes to the preparation of said polymers include
(i) polycondensation
(ii) ring opening/equilibrium
(iii) polyaddition
(iv) chain extension (i) Polycondensation (i.e. the polymerisation of multiple monomers and/or oligomers with the elimination of low molecular weight by-product(s) such as water, ammonia or methanol etc.). Any suitable polycondensation reaction pathway may be utilised.

The sort of reaction envisaged between the condensable end groups of the starting materials are alternatively generally linked to the interaction of compounds having hydroxyl and/or hydrolysable end groups which can interact with the release of e.g. water or methanol or the like. However, the following list indicates other interactions which might be considered for the cure process of the composition in accordance with the present disclosure:
1) the condensation of organohalosilyl groups with an organoalkoxysilyl groups,
2) the condensation of organohalosilyl groups with organoacyloxysilyl groups,
3) the condensation of organohalosilyl groups with organosilanols,
4) the condensation of organohalosilyl groups with silanolates,
5) the condensation of organo-hydrosilyl groups with organosilanol groups
6) the condensation of organoalkoxysilyl groups with organoacyloxysilyl groups
7) the condensation of organoalkoxysilyl groups with organosilanol groups,
8) the condensation of organoaminosilyl groups with organosilanols,
9) the condensation of organoacyloxysilyl groups silanolate groups
10) the condensation of organoacyloxysilyl groups with organosilanols,
11) the condensation of organooximosilyl groups with organosilanol groups
12) the condensation of organoenoxysilyl groups with organosilanols,
13) The condensation of a siloxane compound comprising one or more hydrosilane functional groups with a siloxane compounds containing at least one alkoxysilane functional group, generating hydrocarbon by-products.

Alternatively the condensation reaction may occur between monomers/oligomers and intermediates with hydroxyl and/or alkoxy end-groups thereby producing water or alcohols as a by-product.

A preferred method for the polymerisation process is the polymerisation of straight chain precursors and/or branched organopolysiloxanes of formula (1) including for example $$R_{(3-f)}R^5{}_fSiO(R_2SiO)_gSiR_{(3-f)}R^5{}_f$$

$$R_{(3-f)}R^5{}_fSiO(RR^1SiO)_hSiR_{(3-f)}R^5{}_f$$

$$R_{(3-f)}R^5{}_fSiO[R_2SiO)_j(RR^5SiO)_k]SiR_{(3-f)}R^5{}_f$$

Where R is as previously defined, $R^5$ is —OH or an alkoxy group having from 1 to 6 carbon atoms, alternatively a methoxy or ethoxy group, f is 0 or 1, alternatively 1, g is an integer from 2 to 100, h is from 2 to 100, j is an integer from 1 to 100 and k is an integer between 1 to 100. Some branching may occur with the presence of other groups in the polymeric chain but typically this is kept to a minimum.

The above starting materials alternatively have a viscosity of between 10 mPa·s and 5000 mPa·s at 25° C.

Many of the above processes require the presence of catalyst. Any suitable polycondensation catalyst may be utilised including tin, lead, antimony, iron, cadmium, barium, manganese, zinc, chromium, cobalt, nickel, titanium, aluminium, gallium or germanium and zirconium based catalysts such as organic tin metal catalysts and 2-ethylhexoates of iron, cobalt, manganese, lead and zinc may alternatively be used.

Tin catalysts may include as triethyltin tartrate, tin octoate, tin oleate, tin naphthate, butyltintri-2-ethylhexoate, tinbutyrate, carbomethoxyphenyl tin trisuberate, isobutyltin-triceroate, and diorganotin salts especially diorganotin dicarboxylate compounds such as dibutyltin dilaurate, dimethyltin dibutyrate, dibutyltin dimethoxide, dibutyltin diacetate, dimethyltin bisneodecanoate Dibutyltin dibenzoate, stannous octoate, dimethyltin dineodecanoate, dibutyltin dioctoate. Dibutyltin dilaurate, dibutyltin diacetate are particularly preferred.

Titanate catalysts may comprise a compound according to the general formula Ti[OR$^{20}$]$_4$ and Zr[OR$^{20}$]$_4$ respectively where each R$^{2o}$ may be the same or different and represents a monovalent, primary, secondary or tertiary aliphatic hydrocarbon group which may be linear or branched containing from 1 to 10 carbon atoms. Optionally the titanate may contain partially unsaturated groups. However, preferred examples of R$^{20}$ include but are not restricted to methyl, ethyl, propyl, isopropyl, butyl, tertiary butyl and a branched secondary alkyl group such as 2,4-dimethyl-3-pentyl. Alternatively, when each R°is the same, R°is an isopropyl, branched secondary alkyl group or a tertiary alkyl group, in particular, tertiary butyl. Examples include tetrabutyltitanate, tetraisopropyltitanate, or chelated titanates or zirconates such as for example diisopropyl bis(acetylacetonyl)titanate, diisopropyl bis(ethylacetoacetonyl)titanate, diisopropoxytitanium Bis(Ethylacetoacetate) and the like. Further examples of suitable catalysts are described in EP1254192 and/or WO200149774 the contents of which are incorporated herein by reference. The amount of catalyst used depends on the cure system being used but typically is from 0.01 to 3% by weight of the total composition.

Other condensation catalysts which may be used, protic acids, Lewis acids, organic and inorganic bases, metal salts and organometallic complexes. Lewis acid catalysts. (a "Lewis acid" is any substance that will take up an electron pair to form a covalent bond).suitable for the polymerisation in the present disclosure include, for example, boron trifluoride FeCl$_3$, AlCl$_3$, ZnCl$_2$, and ZnBr$_2$.

More preferred are condensation specific catalysts such as acidic condensation catalysts of the formula R$^{21}$SO$_3$H in which R$^{21}$ represents an alkyl group alternatively having from 6 to 18 carbon atoms such as for example a hexyl or dodecyl group, an aryl group such as a phenyl group or an alkaryl group such as dinonyl- or didodecyl-naphthyl. Water may optionally be added. Alternatively R$^{21}$ is an alkaryl group having an alkyl group having from 6 to 18 carbon atoms such as dodecylbenzenesulphonic acid (DBSA). Other condensation specific catalysts include n-hexylamine, tetramethylguanidine, carboxylates of rubidium or caesium, hydroxides of magnesium, calcium or strontium and other catalysts as are mentioned in the art, e.g. in GB895091, GB918823 and EP 0382365. Also preferred are catalysts based on phosphonitrile chloride, for example those prepared according to U.S. Pat. Nos. 3,839,388, 4,564,693 or EP215470 and phosphonitrile halide ion based catalysts, as described in GB2252975, having the general formula [X(PX$_2$=N)$_p$PX$_3$]$^+$[M$^2$X$_{(m-n+1)}$R$^{III}_m$]$^-$, wherein X denotes a halogen atom, M$^2$ is an element having an electronegativity of from 1.0 to 2.0 according to Pauling's scale, R$^{III}$ is an alkyl group having up to 12 carbon atoms, p has a value of from 1 to 6, m is the valence or oxidation state of M$^2$ and n has a value of from 0 to m−1.

Alternatively the catalyst may comprise an oxygen-containing chlorophosphazene containing organosilicon groups having the following general formula:

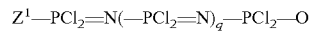
$$Z^1\text{—PCl}_2\text{=N(—PCl}_2\text{=N)}_q\text{—PCl}_2\text{—O}$$

in which
Z$^1$ represents an organosilicon group bonded to phosphorus via oxygen, a chlorine atom or the hydroxyl group and q represents 0 or an integer from 1 to 8. The catalyst may also comprise condensation products of the above and/or tautomers thereof (the catalyst exists in a tautomeric form when Z$^1$ is a hydroxyl group).

A further alternative catalyst which might be used as the catalyst in the present disclosure is any suitable compound providing a source of anions comprising at least one quadrisubstituted boron atom and protons capable of interaction with at least one silanol group as defined in WO 01/79330.

The activity of the catalyst is alternatively quenched by using a neutralizing agent which reacts with the catalyst to render it non-active. Typically in the case of the acid type condensation catalysts the neutralising agent is a suitable base such as an amine such as a mono/di and trialkanolamines for example monoethanolamine (MEA) and triethanolamine (TEA). In the case of systems using a DBSA catalyst alternative quenching means include aluminasilicate zeolite materials that were found to absorb DBSA and leave a stable polymer. In most cases catalyst residues remain in the polymer product or where appropriate may be removed by filtration or alternative methods. In the case of phosphazene based catalysts when the desired viscosity has been reached, the viscosity of the organosilicon compound obtained in the process can be kept constant by a procedure in which the catalyst used, or a reaction product which has been formed from this catalyst by reaction with organosilicon compound to be subjected to condensation and/or equilibration and likewise promotes the condensation and/or equilibration of organosilicon compounds, is inhibited or deactivated by addition of inhibitors or deactivators which have been employed to date in connection with phosphazenes, for example, triisononylamine, n-butyllithium, lithium siloxanolate, hexamethylcyclotrisilazane, hexamethyldisilazane and magnesium oxide.

Where appropriate any suitable end-blocking agent, which halts the polymerization reaction and thereby limits the average molecular weight, may be used to introduce the appropriate end-groups in polymer (a).

(II) Equilibration/Ring Opening

The starting material for equilibration polymerisation processes such as ring-opening polymerisation is a cyclosiloxane (also known as a cyclic siloxane). Cyclic siloxanes which are useful are well known and commercially available materials. They have the general formula (R$^{22}$SiO)$_r$ wherein each R$^{22}$ is selected from an alkyl group, an alkenyl group, an aryl group or an aralkyl group and r denotes an integer with a value of from 3 to 12. R$^{22}$ can contain substitution, e.g. a polar group as hereinbefore described. The alkyl group can be, for example, methyl, ethyl, n-propyl, trifluoropropyl, n-butyl, sec-butyl, and tert-butyl. The alkenyl group can be, for example, vinyl, allyl, propenyl, and butenyl. The aryl and aralkyl groups can be, for example, phenyl, tolyl, and benzoyl. The preferred groups are methyl, ethyl, phenyl, vinyl, and trifluoropropyl. Alternatively at least 80% of all R$^{22}$ groups are methyl or phenyl groups, alternatively methyl. Alternatively the average value of r is from 3 to 6. Examples of suitable cyclic siloxanes are octamethylcyclotetrasiloxane, hexamethylcyclotrisiloxane, decamethylcyclopentasiloxane, cyclopenta(methylvinyl)siloxane, cyclotetra(phenylmethyl)siloxane, cyclopentamethylhydrosiloxane and mixtures thereof. One particularly suitable commercially available material is a mixture of comprising octamethylcyclotetrasiloxane and decamethylcyclopentasiloxane. Typically moisture is present in the monomers. The water present acts as an end-blocker by forming OH end groups on the polymers thereby preventing further polymerisation.

Any suitable catalyst may be used. These include alkali metal hydroxides such as lithium hydroxide, sodium hydroxide, potassium hydroxide or caesium hydroxide, alkali metal alkoxides or complexes of alkali metal hydroxides and an alcohol, alkali metal silanolates such as potassium silanolate caesium silanolate, sodium silanolate and lithium silanolate or trimethylpotassium silanolate. Other catalysts which might be utilised include the catalyst derived by the reaction of a tetra-alkyl ammonium hydroxide and a siloxane tetramer and the boron based catalysts as hereinbefore described.

Catalysts which are most preferred for equilibrium type reactions however are phosphonitrile halides, phosphazene acids and phosphazene bases as hereinbefore described.

Where required the polymer obtained may be end-blocked as a means of regulating the molecular weight of the polymer and/or to add functionality. Whilst this end-blocking function can be achieved by water as discussed above, other suitable end-blocking agents include silanes having one group capable of reacting with the terminal groups of the resulting polymeric constituent prepared in the diluted polymer to produce the required end-groups.

(III) Polyaddition

For the sake of this specification a "polyaddition" or "addition polymerisation" process is a polymerisation process whereby unlike in a condensation reaction no by-products such as water or alcohols are generated from the monomeric and oligomeric co-reactants during polymerisation. A preferred addition polymerisation route is a hydrosilylation reaction between an unsaturated organic group e.g. an alkenyl or alkynyl group and an Si—H group in the presence of a suitable catalyst. In this route suitable silanes may be utilised as well as siloxane containing monomers and/or oligomers.

Typically the polyaddition route is utilised to form block copolymers by reacting
(i) an organopolysiloxane or
(ii) a silane with one or more organopolysiloxane polymer(s) via an addition reaction pathway in the presence of the inert fluid (e.g. extender and/or plasticiser), a suitable catalyst and optionally an end-blocking agent and where required quenching the polymerisation process.

The organopolysiloxane or silane (a) is selected from:
(a) (ii) a silane containing at least one group capable of undergoing addition type reactions and (a) (i) an organopolysiloxane monomer containing groups capable of undergoing addition type reactions.

The organopolysiloxane or silane (a) must contain substituents such that it is capable of undergoing an appropriate addition reaction with polymer (b). The preferred addition reaction is a hydrosilylation reaction between an unsaturated group and an Si—H group.

Preferably silane (a) (ii) has at least 1 and alternatively 2 groups capable of undergoing addition type reactions with (b). When the addition reaction is a hydrosilylation reaction the silane may contain an unsaturated constituent but preferably contains at least one Si—H group. Alternatively each silane contains one or more Si—H groups. In addition to the one or more Si—H groups, preferred silanes may include for example an alkyl group, an alkoxy group, an acyloxy group, a ketoximato group, an amino group, an amido group, an acid amido group, an aminoxy group, a mercapto group, an alkenyloxy group and the like. Among these, alkoxy, acyloxy, ketoximato, amino, amido, aminoxy, mercapto and alkenyloxy groups are preferred. Practical examples of the silicon hydride are halosilane tri-chlorosilane, methyl dichlorosilane, dimethyl chlorosilane, and phenyl dichlorosilane; alkoxy silanes, such as tri-methyoxy silane, tri-ethoxy silane, methyl di-ethoxy silane, methyl di-methoxy silane and phenyl-di-methoxy silane; acyloxy silanes, such as methyl di-acetoxy silane and phenyl diacetoxy silane; and ketoximato silanes, such as bis-(dimethyl-ketoximate)-methyl silane and bis-(cyclohexyl ketoximate)methyl silane. Among them, halosilanes and alkoxyl silanes are preferred. Particularly preferred silanes include for example methyl dimethoxy silane (H—Si(—CH$_3$)(—OCH$_3$)$_2$).

It will be appreciated that the addition reaction between silane (a) (ii) and (b) results in a polymer chain extension process or as a means of end-blocking a polymer with pre-required end groups, in which case the extender may be added in combination with silane (a) (ii), i.e. immediately prior to the addition reaction or may be present during the polymerisation of polymer (b) and as such silane (a) (ii) is added to an extended polymer (b) which has been polymerised in the presence of the extender.

Organopolysiloxane monomer (a) (i) is alternatively in the form of a straight chain monomer but may have some branching an is an organopolysiloxane comprising units of formula (1a)

$$R'_a SiO_{4-a/2} \quad (1a)$$

wherein each R' may be the same or different and denotes a hydrocarbon group having from 1 to 18 carbon atoms, a substituted hydrocarbon group having from 1 to 18 carbon atoms or a hydrocarbonoxy group having up to 18 carbon atoms and a' has, on average, a value of from 1 to 3, alternatively 1.8 to 2.2. Alternatively each R' is the same or different and is exemplified by, but not limited to hydrogen, alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. Alternatively at least some of the R' groups contain polar substitution. Alternatively the polydiorganosiloxanes are polydialkylsiloxanes, or alternatively polydimethylsiloxanes. When (a) is an organopolysiloxane monomer, said organopolysiloxane monomer must have at least one group which is reactable with at least two groups, typically the terminal groups, of (b) via an addition reaction process. Alternatively organopolysiloxane (a) (i) comprises at least one Si—H per molecule, alternatively at least two Si—H groups per molecule. Alternatively organopolysiloxane (a) (i) is end-blocked with a siloxane group of the formula H(R")$_2$SiO$_{1/2}$, wherein each R" is a hydrocarbon or substituted hydrocarbon group, alternatively an alkyl group. Alternatively organopolysiloxane (a) (i) has a viscosity of between 10 mPa·s and 5000 mPa·s at 25° C.

Organopolysiloxane polymer (b) is alternatively a straight chain and/or branched organopolysiloxane comprising units of formula (1b)

$$R'''_a SiO_{4-a/2} \quad (1b)$$

wherein each R''' may be the same or different and denotes a hydrocarbon group having from 1 to 18 carbon atoms, a substituted hydrocarbon group having from 1 to 18 carbon atoms or a hydrocarbonoxy group having up to 18 carbon atoms and a' is as previously described. Preferably no R''' groups may be hydrogen groups. Alternatively each R''' is the same or different and are exemplified by, but not limited to alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl.

Organopolysiloxane polymer (b) may comprise any suitable organopolysiloxane polymeric backbone but is alternatively linear or branched, and comprises at least one, alternatively at least two substituent groups which will react with the aforementioned groups in the organopolysiloxane or silane (a) via an addition reaction pathway. Preferably the or each addition reactive substituent group of polymer (b) is a terminal group. When the organopolysiloxane or silane (a) comprises at least one Si—H group, the preferred substituent groups on organopolysiloxane polymer (b), which are designed to interact with the Si—H groups, are alternatively unsaturated groups (e.g. alkenyl terminated e.g. ethenyl terminated, propenyl terminated, allyl terminated ($CH_2$=$CHCH_2$—)) or terminated with acrylic or alkylacrylic such as $CH_2$=$C(CH_3)$—$CH_2$— groups Representative, non-limiting examples of the alkenyl groups are shown by the following structures; $H_2C$=$CH$—, $H_2C$=$CHCH_2$—, $H_2C$=$C(CH_3)CH_2$—, $H_2C$=$CHCH_2CH_2$—, $H_2C$=$CHCH_2CH_2CH_2$—, and $H_2C$=$CHCH_2CH_2CH_2CH_2$—. Representative, non-limiting examples of alkynyl groups are shown by the following structures; $HC$≡$C$—, $HC$≡$CCH_2$—, $HC$≡$CC(CH_3)$—, $HC$≡$CC(CH_3)_2$—, $HC$≡$CC(CH_3)_2CH_2$— Alternatively, the unsaturated organic group can be an organo functional hydrocarbon such as an acrylate, methacrylate and the like such as alkenyl an/or alkynyl groups. Alkenyl groups are particularly preferred.

In cases where the organopolysiloxane or silane (a) comprises only one addition reactable group and (b) comprises two addition reactable groups which will react with the organopolysiloxane or silane (a), the resulting product will be an "ABA" type polymeric product. Whereas when both the organopolysiloxane or silane (a) comprises two addition reactable groups and (b) comprises two addition reactable groups which will react with the organopolysiloxane or silane (a) interaction between the two components would lead to (AB)n block copolymers in which the length of the polymer is largely determined by the relative amounts of the two constituents.

It will also be appreciated that this hydrosilylation route may be utilised to prepare silicone-organic copolymers by using an organopolysiloxane polymer which contains organic groups in the polymer backbone or by replacing organopolysiloxane polymer (b) with, for example alkenyl terminated polyethers Hence linear non-hydrolysable (AB)n block copolymers in accordance with the present disclosure of this disclosure can be prepared by catalyzed hydrosilylation of alkenyl terminated polyethers with SiH-terminated dialkylsiloxane fluids. The resulting copolymer being a combination of polyoxyalkylene blocks linked through silicon to carbon to oxygen linkages (i.e. a propyleneoxy group) and the endblocking groups being selected from the group consisting of allyl, propenyl and/or hydrogen (dialkyl) siloxy groups (dependent on the relative amounts of the constituents which are present).

When the addition reaction chosen is a hydrosilylation reaction, any suitable hydrosilylation catalyst may be utilised. Such hydrosilylation catalysts are illustrated by any metal-containing catalyst which facilitates the reaction of silicon-bonded hydrogen atoms of the SiH terminated organopolysiloxane with the unsaturated hydrocarbon group on the polyoxyethylene. The metals are illustrated by ruthenium, rhodium, palladium, osmium, iridium, or platinum.

Hydrosilylation catalysts are illustrated by the following; chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum supported on metal oxide carriers such as $Pt(Al_2O_3)$, platinum black, platinum acetylacetonate, platinum(divinyltetramethyldisiloxane), platinous halides exemplified by $PtCl_2$, $PtCl_4$, $Pt(CN)_2$, complexes of platinous halides with unsaturated compounds exemplified by ethylene, propylene, and organovinylsiloxanes, styrene hexamethyldiplatinum, Such noble metal catalysts are described in U.S. Pat. No. 3,923,705, incorporated herein by reference to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. Most preferred as the catalyst is a neutralized complex of platinous chloride and divinyl tetramethyl disiloxane, for example as described in U.S. Pat. No. 5,175,325.

Ruthenium catalysts such as $RhCl_3(Bu_2S)_3$ and ruthenium carbonyl compounds such as ruthenium 1,1,1-trifluoroacetylacetonate, ruthenium acetylacetonate and triruthinium dodecacarbonyl or a ruthenium 1,3-ketoenolate may alternatively be used.

Other hydrosilylation catalysts suitable for use in the present disclosure include for example rhodium catalysts such as $[Rh(O_2CCH_3)_2]_2$, $Rh(O_2CCH_3)_3$, $Rh_2(C_8H_{15}O_2)_4$, $Rh(C_5H_7O_2)_3$, $Rh(C_5H_7O_2)(CO)_2$, $Rh(CO)[Ph_3P]$ $(C_5H_7O_2)$, $RhX^4_3[(R^3)_2S]_3$, $(R^2_3P)_2Rh(CO)X^4$, $(R^2_3P)_2Rh$ $(CO)H$, $Rh_2X^4_2Y^4_4$, $H_aRh_b olefin_c Cl_d$, $Rh$ $(O(CO)R^3)_{3-n}$ $(OH)_n$ where $X^4$ is hydrogen, chlorine, bromine or iodine, $Y^4$ is an alkyl group, such as methyl or ethyl, CO, $C_8H_{14}$ or 0.5 $C_8H_{12}$, $R^3$ is an alkyl group, cycloalkyl group or aryl group and $R^2$ is an alkyl group an aryl group or an oxygen substituted group, a is 0 or 1, b is 1 or 2, c is a whole number from 1 to 4 inclusive and d is 2,3 or 4, n is 0 or 1. Any suitable iridium catalysts such as $Ir(OOCCH_3)_3$, $Ir(C_5H_7O_2)_3$, $[Ir(Z^2)(En)_2]_2$, or $(Ir(Z^2)(Dien)]_2$, where $Z^2$ is chlorine, bromine, iodine, or alkoxy, En is an olefin and Dien is cyclooctadiene may also be used.

The hydrosilylation catalyst may be added to the present composition in an amount equivalent to as little as 0.001 part by weight of elemental platinum group metal, per one million parts (ppm) of the composition. Alternatively, the concentration of the hydrosilylation catalyst in the composition is that capable of providing the equivalent of at least 1 part per million of elemental platinum group metal. A catalyst concentration providing the equivalent of about 3-50 parts per million of elemental platinum group metal is generally the amount preferred.

Typically when (a) has at least two Si—H groups, typically, the process is carried out using approximately a 1:1 molar ratio of (a) to (b). However, useful materials may also be prepared by carrying out the process with an excess of either (a) or (b) but this would be considered a less efficient use of the materials. Typically, the material containing the unsaturation (b) is used in slight excess to ensure all the Si—H is consumed in the reaction. As polymer (b) used in the present disclosure is alternatively terminated with unsaturated end-groups, end-blocking agents are not typically required when making the polymer via this route. However, they may be utilised if required.

Optionally when a hydrosilylation route is utilised for polymerisation a suitable hydrosilylation catalyst inhibitor may be required. Any suitable platinum group type inhibitor may be used. One useful type of platinum catalyst inhibitor is described in U.S. Pat. No. 3,445,420, which is hereby incorporated by reference to show certain acetylenic inhibitors and their use. A preferred class of acetylenic inhibitors are the acetylenic alcohols, especially 2-methyl-3-butyn-2-ol and/or 1-ethynyl-2-cyclohexanol which suppress the activity of a platinum-based catalyst at 25° C. A second type of platinum catalyst inhibitor is described in U.S. Pat. No. 3,989,667, which is hereby incorporated by reference to show certain olefinic siloxanes, their preparation and their use as platinum catalyst inhibitors. A third type of platinum catalyst inhibitor includes polymethylvinylcyclosiloxanes having three to six methylvinylsiloxane units per molecule.

Compositions containing these hydrosilylation catalysts typically require heating at temperatures of 70° C. or above to cure at a practical rate, particularly if an inhibitor is used. Room temperature cure is typically accomplished with such systems by use of a two-part system in which the cross-linker and inhibitor are in one of the two parts and the platinum is in the other part. The amount of platinum is increased to allow for curing at room temperature. The optimum concentration of platinum catalyst inhibitor is that which will provide the desired storage stability or pot life at ambient temperature without excessively prolonging the time interval required to cure the present compositions at elevated temperatures. This amount will vary widely and will depend upon the particular inhibitor that is used. Inhibitor concentrations as low as one mole of inhibitor per mole of platinum will in some instances yield a desirable level of storage stability and a sufficiently short curing period at temperatures above about 70° C. In other cases, inhibitor concentrations of up to 10, 50, 100, 500 or more moles per mole of platinum may be needed. The optimum concentration for a particular inhibitor in a given composition can be determined by routine experimentation.

Additional components can be added to the hydrosilylation reaction which are known to enhance such reactions. These components include salts such as sodium acetate which have a buffering effect in combination with platinum based catalysts.

For this type of polymerisation the amount of hydrosilylation catalyst used is not narrowly limited as long as there is a sufficient amount to accelerate a reaction between (a) (i) an organopolysiloxane or (ii) a silane the chosen of which must contain at least one and alternatively at least two Si—H groups with (b) one or more organopolysiloxane polymer(s) or an alternative therefore such as a polyoxyethylene having an unsaturated hydrocarbon group at each molecular terminal at room temperature or at temperatures above room temperature. The actual amount of this catalyst will depend on the particular catalyst utilized and is not easily predictable. However, for platinum-containing catalysts the amount can be as low as one weight part of platinum for every one million weight parts of components (a) and (b). The catalyst can be added at an amount 10 to 120 weight parts per one million parts of components (a) and (b), but is typically added in an amount from 10 to 60 weight parts per one million parts of (a) and (b)

Where appropriate, polymers obtained via a hydrosilylation route can also be cured and/or crosslinked by a hydrosilylation reaction catalyst in combination with an organohydrogensiloxane as the curing agent providing each polymer molecule produced contains at least two unsaturated groups suitable for cross-linking with the organohydrogensiloxane. To effect curing of the present composition, the organohydrogensiloxane must contain more than two silicon bonded hydrogen atoms per molecule. The organohydrogensiloxane can contain, for example, from about 4-20 silicon atoms per molecule, and have a viscosity of up to about 10 Pa·s at 25° C.

The silicon-bonded organic groups present in the organohydrogensiloxane can include substituted and unsubstituted alkyl groups of 1-4 carbon atoms that are otherwise free of ethylenic or acetylenic unsaturation.

(IV) Chain Extension

In this case rather than adding chain extender into a final pre-prepared polymer composition the extender is mixed into the polymer during a chain extension polymerisation step. Typically the polymeric starting material is an organopolysiloxane having end groups suitable for interaction with the chosen chain extending materials. Typically the polymer end groups are either hydrolysable or suitable for addition reaction (typically hydrosilylation) and the chain extending material is chosen on the basis of having suitable reactive groups which will chain extend the polymer. Preferred chain extending materials for chain extending polymers having hydroxyl and/or hydrolysable end groups are as hereinbefore described.

For pre-formed polymers with alkenyl or Si—H groups (typically end groups) suitable for addition reactions via a hydrosilylation route the chain extender will contain two groups which will undergo an addition reaction with the respective addition reactive groups on the chosen polymer. Such chain extenders may include for example:

A silane comprising two alkenyl groups, a dihydrosilane, a polydialkylsiloxane having a degree of polymerisation of from 2 to 25 and at least one Si-alkenyl bond per terminal group, A polydialkylsiloxane having a degree of polymerisation of from 2 to 25 and at least one Si—H bond per terminal group and wherein each alkyl group independently comprises from 1 to 6 carbon atoms;

organosilicon compounds with the general formula

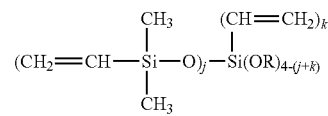

in which R is as hereinbefore described, j is 1, 2, or 3, k is 0 or 1, and j+k is 2 or 3.

These are exemplified by compounds with the following formulas, (ViMe$_2$SiO)$_2$SiVi(OMe)$_1$, (ViMe$_2$SiO)$_1$SiVi(OMe)$_2$, (ViMe$_2$SiO)$_2$SiVi(OEt)$_1$, (ViMe$_2$SiO)$_1$SiVi(OEt)$_2$, (ViMe$_2$SiO)$_3$Si(OMe)$_1$, (ViMe$_2$SiO)$_2$Si(OMe)$_2$, (ViMe$_2$SiO)$_3$Si(OEt)$_1$ and (ViMe$_2$SiO)$_2$Si(OEt)$_2$.

As used herein, Vi represents a vinyl group, Me represents a methyl group, and Et represents an ethyl group.

The catalyst used to catalyse the chain extension reaction is determined by the reaction to take place. When the reaction occurring is a condensation reaction any suitable condensation catalyst as hereinbefore described may be utilised. When the reaction occurring is a hydrosilylation reaction any suitable hydrosilylation catalyst as hereinbefore described may be utilised.

Where required the polymer contains hydrolysable terminal groups, end-blocking agents as described above in relation to condensation may be utilised to obtain appropriate terminal groups. Where required the polymer contains addition reactable terminal groups, end-blocking agents as described above in relation to polyaddition may be utilised to obtain appropriate terminal groups.

The process can be carried out either batchwise or continuously on any suitable mixers. In case of a polycondensation, generated water can either be removed by chemical drying using e.g. hydrolysable silanes like methyltrimethoxysilane or by physical separation using evaporation, coalescing or centrifuging techniques.

Chain extension may take place at any suitable temperature and pressure for the process concerned in batch or continuous modes of operation as preferred. Hence in the case of the phosphazene catalysed methods polymerisation may occur at temperatures of between 50° C. to 200° C., or alternatively 80° C. to 160° C. Furthermore, in order to facilitate removal of the by-products formed during the condensation, for example, water, HCl or alcohol, the condensation and/or equilibration of the organosilicon compounds may be carried out at a pressure below 80 kPa. Alternative methods for the removal of condensation by-products include removal by chemical drying using e.g. hydrolysable silanes like methyltrimethoxysilane (where appropriate) or by physical separation using evaporation, coalescing or centrifuging techniques.

The process can be carried out either batchwise or continuously on any suitable mixers. In case of a polycondensation, generated water can either be removed by chemical drying using e.g. hydrolysable silanes like methyltrimethoxysilane or by physical separation using evaporation, coalescing or centrifuging techniques.

It is to be appreciated that a combination of two different reactions according to the above may also be employed to make the polysiloxane polymer according to the present invention. For example, a ring-open/equilibration reaction may be followed by a polyaddition reaction, both in the presence of the inert fluid, in achieving the final polysiloxane polymer and the inert fluid mixture.

The extent of polymerization during the process of the invention is preferably such that the organopolysiloxane of increased molecular weight produced has a weight average molecular weight (Mw) of at least five times, more preferably at least ten times the weight average molecular weight of the starting organopolysiloxane. The Mw can be measured by gel permeation chromatography (GPC). The Mw of the organopolysiloxane of increased molecular weight produced is preferably at least 10,000, more preferably at least 100,000, and may be as high as 1,000,000 or more.

Typically the viscosity of the mixture of the polysiloxane polymer and inert fluid prior to emulsifying is in the range of viscosity of 100-100000 mPa·s at 25° C., alternatively the viscosity of the polysiloxane polymer in the emulsion is greater than 1 000 mPa·s at 25° C.

One or more surfactants can be used in the present disclosure. These may be selected from suitable classes of surfactant including the anionic, cationic, nonionic or amphoteric type. While not to be restricted, a combination of two surfactants is more effective in making stable emulsions, in this case an anionic with a nonionic, a cationic with a nonionic, or two nonionic surfactants is suitable. The general principle is to have one surfactant more soluble in the oil phase (low hydrophilic-lipophilic-balance (HLB)) and another more soluble in the water phase (high HLB) with a combined affinity more towards the aqueous phase (an overall HLB greater than 10).

Any suitable surfactant or combination of surfactants consistent with the above may be utilised. The surfactant can in general be a non-ionic surfactant, a cationic surfactant, an anionic surfactant, or an amphoteric surfactant, although not all procedures for carrying out the process of the invention can be used with all surfactants. The amount of surfactant used will vary depending on the surfactant. For microemulsions, this can be up to or even greater than the weight of the oil phase, but high amount of surfactant will reduce the economic value of the product in commerce. Generally one uses as low amount of surfactant as possible for a targeted emulsion particle size. A preferred and practical amount is 5 to 50% based on the weight of the oil phase including the polysiloxane and the inert fluid.

Examples of nonionic surfactants include but are not restricted to condensates of ethylene oxide with long chain fatty alcohols or fatty acids such as a $C_{12-18}$ or alternatively $C_{12-16}$ alcohol, condensates of ethylene oxide with an amine or an amide, polyoxyethylene alkyl phenyl ethers, polyoxyethylene fatty acid esters, sorbitan fatty acid esters and polyoxyethylene sorbitan fatty acid esters, condensation products of ethylene and propylene oxide, esters of glycerol, sucrose, sorbitol, fatty acid alkylol amides, sucrose esters, fluoro-surfactants, fatty amine oxides, polyoxyalkylene alkyl ethers such as polyethylene glycol long chain (12-18C, alternatively 12-16C) alkyl ether, polyoxyalkylene sorbitan ethers, polyoxyalkylene alkoxylate esters, polyoxyalkylene alkylphenol ethers, ethylene glycol propylene glycol copolymers and alkylpolysaccharides, for example materials of the structure $R^{24}$—O—$(R^{25}O_s$-$(G)_t$ wherein $R^{24}$ represents a linear or branched alkyl group, a linear or branched alkenyl group or an alkylphenyl group, $R^{25}$ represent an alkylene group, G represents a reduced sugar, s denotes 0 or a positive integer and t represent a positive integer as described in U.S. Pat. No. 5,035,832. non ionic surfactants additionally include polymeric surfactants such as polyvinyl alcohol (PVA) and polyvinylmethylether.

Representative examples of suitable commercially available nonionic surfactants include polyoxyethylene fatty alcohols sold under the tradename BRIJ® by Uniqema (ICI Surfactants), Wilmington, Del. Some examples are BRIJ® 35, an ethoxylated alcohol known as polyoxyethylene (23) lauryl ether, and BRIJ® 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40. Surfactants containing silicon atoms can also be used. Other suitable nonionic surfactant according to the present disclosure are commercially available under the names ALFONIC®, GENAPOL®, LUTENSOL®, NEODOL®, RENEX, SOFTANOL, SURFONIC®, TRYCOL AND VOLPO.

Examples of suitable amphoteric surfactants include imidazoline compounds, alkylaminoacid salts, and betaines. Specific examples include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds. Representative examples of suitable amphoteric surfactants include imidazoline compounds, alkylaminoacid salts, and betaines.

Examples of cationic surfactants include, but are not restricted to, quaternary ammonium hydroxides such as octyl trimethyl ammonium hydroxide, dodecyl trimethyl ammonium hydroxide, such as alkyl trimethylammonium and dialkyldimethylammonium halides or acetates or hydroxides having at least 8 carbon atoms in each alkyl substituent, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines. Other representative examples of suitable cationic surfactants include alkylamine salts, sulphonium salts, and phosphonium salts.

Examples of suitable anionic surfactants include but are not restricted to, sulfonic acids and their salts including alkyl, alkylaryl, alkylnapthalene, and alkyldiphenylether sulfonic acids and their salts having at least 6 carbon atoms in the alkyl substituent, such as dodecylbenzensulfonic acid and its sodium or amine salt; the sulfate esters of polyoxyethylene monoalkyl ethers; long chain carboxylic acid surfactants and their salts such as lauric acid, steric acid, oleic acid and their alkali metal and amine salts, alkyl sulphates such as lauryl sulphate, polymers such as acrylates/$C_{10-30}$ alkyl acrylate crosspolymer alkylbenzenesulfonic acids and salts such as hexylbenzenesulfonic acid, octylbenzenesulfonic acid, decylbenzenesulfonic acid, dodecylbenzenesulfonic acid, cetylbenzenesulfonic acid and myristylbenzenesulfonic acid; the sulphate esters of monoalkyl polyoxyethylene ethers; alkylnapthylsulfonic acid; alkali metal sulforecinates, sulfonated glyceryl esters of fatty acids such as sulfonated monoglycerides of coconut oil acids, salts of sulfonated monovalent alcohol esters, amides of amino sulfonic acids, sulfonated products of fatty acid nitriles, sulfonated aromatic hydrocarbons, condensation products of naphthalene sulfonic acids with formaldehyde, sodium octahydroanthracene sulfonate, alkali metal alkyl sulphates, ester sulphates, and alkarylsulfonates. Anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft® N-300. Bio-Soft$^{(R)}$ N-300 is a triethanolamine linear alkylate sulphonate composition marketed by the Stephan Company, Northfield, Ill.

The above surfactants may be used individually or in combination.

In a preferred embodiment of the present disclosure the polymerisation catalyst is selected with a view to additionally being the or one of the surfactants involved in the emulsification process. A particularly preferred family of catalysts which can act as surfactants are acidic condensation catalysts such as for example DBSA.

The specific amount of surfactant employed in the microemulsion according to the present disclosure is not critical but should be such as to result in a stable microemulsion. Generally this should amount to a sufficient amount of surfactant molecules to cover the interfacial area of the oil-water droplets in the microemulsion, but not much more than providing a monolayer coverage. While not to be bound to theory, generally, 2 to 100 wt percent of surfactant based on weight of the oil phase (polysiloxane plus inert fluid) is suitable, alternatively 5 to 50%, or alternatively 20 to 50%, in order to arrive at a microemulsion with particle size less than 140 nanometer. One skilled in the art recognizes that the smaller the particle size, the more the surfactant needed.

A microemulsion according to the present disclosure is made by mixing the oil phase containing the polysiloxane, obtained from polymerization of siloxane or silane containing monomers and/or oligomers in the presence of an inert fluid, with the aforementioned inert fluid, and one or more surfactants till homogeneous, and adding water to the mixture containing the oil phase and surfactant while subjecting the mixture to agitation, to arrive at an oil-in-water microemulsion. Alternatively, the surfactant or surfactants to be employed can be first dissolved or dispersed in an appropriate amount of water to be added to the oil phase, and the surfactant containing water phase is added to the oil phase under agitation to arrive at an oil-in-water microemulsion. Additional water can then be added to dilute the microemulsion. Still alternatively, if more than one surfactant is used, the more oil soluble surfactant can be first combined with the oil phase, the more water soluble surfactant combined with the water phase, and then the water phase is added to the oil phase under agitation to arrive at an oil-in-water microemulsion.

The agitation or homogenization used to emulsify the composition in accordance with the present invention may be by any suitable mechanical means, such as by use of homogenisers, sonolators, rotor stators, colloid mills and the like.

While not wishing to be bound to any particular process condition, one skilled in the art recognizes that certain ways and quantitative combinations of the oil phase, surfactant and water phase work more effective than others in arriving at an emulsion of the smallest possible particle size. A preferred method according to the present disclosure for the microemulsification part comprises the following steps:

i) Combine the oil phase containing the polysiloxane and the inert fluid with the surfactant(s) and mix till homogeneous ii) Add a sufficient amount of water to the oil phase containing the surfactant(s), and mix the content with vigorous agitation to obtain a translucent or transparent mixture iii) Disperse the above translucent or transparent mixture in sufficient amount of water to arrive at an oil-in-water microemulsion iv) Optionally dilute the microemulsion in additional water till a desired oil phase content (solid content) is reached.

In step ii), "sufficient amount" of water is a quantity that would result in the mixture being translucent or transparent. Less than that, an opaque mixture would result. One needs to target an amount of water just sufficient, but not much more, to arrive at a translucent to transparent mixture of the oil phase, surfactant and water. This translucent or transparent mixture is typically of high viscosity or gel-like. Generally, the amount of water is 5 to 100% based on the weight of the oil phase (not including the surfactant). The amount of water needed to form a clear oil concentrate will depend upon the specific polyorganosiloxane and surfactant used as well as their relative amounts. Typically, the amount of water required to form a translucent oil concentrate will be in the range of 5 to 50 parts by weight per 100 parts by weight of the oil phase. Specific polyorganosiloxane and surfactant combinations may require more or less water to form a translucent oil concentrate than these general guidelines suggest. "Vigorous agitation" can be brought by a number of different mixing devices, such as the impeller type mixers, high speed spinning cups, and rotor-stator shear devices.

In step iii), the translucent or transparent mixture resulting from step ii) can be added in whole or in increments to a sufficient amount of water with the water phase under constant agitation. Alternatively, the water is added rapidly to the translucent or transparent mixture from step ii) followed by mixing the resultant content till all the translucent or transparent mixture is completely dispersed in the water. The exact amount of water in which the translucent or transparent mixture from step ii) is dispersed in is not critical, so long as there is sufficient water that the resulting emulsion is an oil-in-water type; but one should avoid titrating the translucent or transparent mixture with water.

The final microemulsion may contain from 5 percent to 55 percent by weight of the oil phase based on the total weight of the emulsion. Typically, the microemulsions of this disclosure contain 10 to 40 weight percent of the oil phase. Microemulsions with less oil phase content can be prepared but such emulsions may prove economically unattractive.

Alternatively, the microemulsion according to the present invention can be prepared by combining the oil phase containing the polysiloxane and the inert fluid, the surfactant(s) and the water, heating the oil, surfactant, water mixture to above the cloud point of the surfactant to make a water-in-oil emulsion, and subsequently cool the water-in-oil emulsion to induce a phase transition arriving at an oil-in-water microemulsion.

In one embodiment there is provided a process according to the present disclosure for the preparation of an amino-functional polysiloxane comprises reacting an aminosilane (A) which contains an aminoalkyl group and at least one alkoxy group bonded to Si with a carboxylic acid (C) and a silanol-functional polysiloxane (B), in the presence of an inert fluid; the amount of carboxylic acid (C) being such that the molar ratio of carboxylic acid groups of (C) to amino groups of aminosilane (A) is less than 1:1 and the amount of silanol-functional polysiloxane (B) being such that the molar ratio of silanol groups of (B) to Si-bonded alkoxy groups of aminosilane (A) is greater than 1:1, whereby the aminosilane (A) is at least partially converted into its carboxylate salt which acts as a catalyst for the siloxane condensation polymerization reaction between (A) and (B).

Microemulsions as provided in the present disclosure are generally more stable against creaming or sedimentation than standard emulsions and in many applications, such as in clear personal care or cosmetic products, provide the required optical transparency. In other applications, deposition and penetration of emulsion into substrate, such as in woven textile applications are enhanced through use of a microemulsion due to the small particle size.

EXAMPLES

The following Examples are provided so that one skilled in the art will more readily understand the disclosure. Unless otherwise indicated, all parts and percents are by weight and all viscosities are at 25° C. Viscosity measurements of the polymer products were carried out using a Brookfield Viscometer, spindle 6, at a speed of 10 rpm.

Example 1

Part A

In a 3 litre three-neck round bottom flask equipped with a stir rod attached with a 11 cm Teflon paddle, a thermocouple, and a condenser was mixed 986.4 grams of decamethylcyclopentasiloxane, 8.4 grams of a trimethylsiloxy-terminated methylhydrogensiloxane of 60 degrees of polymerization, 5.10 grams of hexamethyldisiloxane and 100 grams of a C12-15 alkylbenzoate. The mixture was henceforth covered under nitrogen blanket. To the mixture was added 1 gram of trifluoromethanesulfonic acid via a syringe. The content was heated to and held at 65° C. under constant stir at 300 RPM for four hours. 40 grams of sodium bicarbonate ($NaHCO_3$) was then added and the mixture was cooled to 20° C. The mixture was filtered using a 10 micron filter paper to remove $NaHCO_3$ and was then heated to 120° C. and stripped under vacuum to remove volatile cyclic siloxane. This resulted in a clear mixture containing 90 wt % of a siloxane polymer of 348 degrees of polymerization, as measured by $^{29}Si$ NMR, and 10 wt % of C12-15 alkylbenzoate which was the inert fluid.

Part B

In a 1 litre three-neck round bottom flask equipped with a stir rod attached with a 11 cm Teflon paddle, a thermocouple, a condenser was mixed 195 grams of the product from Part A, 22.2 grams of a poly((ethylene oxide)$_{10}$(propylene oxide)$_4$) monoallyl ether, 10 grams of isopropanol and 0.1 gram of sodium acetate. The mixture was stirred at 300 RPM and heated to 70° C. under nitrogen blanket. To the mixture was added 0.22 gram of a Dow Corning trade secret platinum complex containing 1% of elemental platinum. The reaction was exothermic. The mixture was kept at 84° C. under constant stir for 1 hour and 15 minutes and was then cooled to 40° C. A vacuum was applied to strip off isopropanol in the mixture. The final product contains 91 wt % of a trimethylsiloxy-terminated polydimethyl methyl(propyl(poly(EO)(PO)acetate)siloxane and 9 wt % of C12-15 alkylbenzoate which was the inert fluid.

Part C

To 12 grams of the product from Part B was added 2.5 grams of Genapol® UD050, 3.5 grams of Genapol® UD110 and 5.0 grams of water. The mixture was mixed in a SpeedMixer™ (DAC 150 FVZ) at 3500 RPM for 30 seconds. 12 grams of water was then added in two portions to the mixture and each addition was followed by the same mixing procedure as before. This resulted in a clear (transparent) oil-in-water microemulsion having a mono-modal particle size distribution centered around 30.8 nanometers diameter with 90% of the particles falling below 46.7 nanometers, as measured by a Nanotrac™ particle sizer in volume mode.

Part D

To 10 grams of the product from Part B was added 2.0 grams of Hostapur® SAS-30 (30% active surfactant), 3.0 grams of Genapol® UD050 and 3.5 grams of water. The mixture was mixed in a SpeedMixer™ (DAC 150 FVZ) at 3500 RPM for 30 seconds. 12 grams of water was then added in two portions to the mixture and each addition was followed by the same mixing procedure as before. This resulted in a water clear (transparent) oil-in-water microemulsion having a mono-modal particle size distribution centered around 15.4 nanometers diameter with 90% of the particles falling below 25.1 nanometers, as measured by a Nanotrac™ particle sizer in volume mode.

In this example, a polysiloxane was polymerized in the presence of an organic inert fluid (C12-15 alkylbenzoate) via ring open/equilibration (Part A) followed by polyaddition (Part B). The resultant polymer mixture retaining the inert fluid was then emulsified into a microemulsion using non-ionic surfactant (Part C) and a microemulsion using anionic surfactant (Part D). The benefit of using the inert fluid in this example was to keep the viscosity of the product in Part A low enough to ease the strip of the volatiles as well as for the ease in emulsification, since the polysiloxane had a high degree of polymerization hence a high viscosity. Furthermore, the inert fluid itself can bring added performance benefit as it is often used as an emollient or moisturizer in cosmetic products.

Example 2

A mixture of 80 g dimethyl hydroxyl terminated polydimethylsiloxane having a viscosity of 70 mPa·s at 25° C., 20 g of Hydroseal® G 250H, 3 g of octanoic acid and 6 g of 3-aminopropylmethyldiethoxysilane were mixed with a magnetic stirrer for 24 hours at room temperature (RT). 9 g Lutensol® T08 was added to 15 g of the mixture described above and mixed for 20 s at 3000 rpm in a Hausschild dental mixer. An additional 1.0 g of water was added and mixing repeated under the same conditions. Further additions of water and subsequent mixing were carried out until 26 g water had been added in total, yielding a clear gel with 30% active content. Further dilution in water to 3% active content yielded a clear slightly bluish emulsion which had a particle size of D(v, 0.1) nm=61.1, D(v, 0.5) nm=100.2 (Measured with a Nanotrac particle sizer in the volume mode).

Example 3

A mixture of 80.0 g dimethyl hydroxyl terminated polydimethylsiloxane having a viscosity of 70 mPa·s at 25° C., 20 g of Hydroseal® G 250H, 3.1 g of octanoic acid and 6.0 g of 3-aminopropylmethyldiethoxysilane were mixed with a magnetic stirrer for 24 hours at a temperature of 50° C. The resulting homogenous mixture had a viscosity of 7400 mPas (using a Brookfield RVDV-I+ viscometer Spindle 5, at a speed of 20RPM) at 25° C.

6.1 g Lutensol® T08 was mixed into 15 g of the resulting mixture described above and mixed for 20 s at 3000 rpm in a Hausschild dental mixer. An additional 1.1 g of water was added and mixing repeated under the same conditions. Further sequential additions of water took place with subsequent mixing in each instance until 26 g water had been added in total, yielding a microemulsion with 30% active content which had a particle size of D(v, 0.1) nm=63.3, D(v, 0.5) nm=94.6 (Measured using a Nanotrac particle sizer in the volume mode).

Example 4

A mixture of 80.0 g dimethyl hydroxyl terminated polydimethylsiloxane having a viscosity of 70 mPa·s at 25° C., 20 g of Isopar® L (supplied by Exxon), 3.0 g of octanoic acid and 6.0 g of 3-aminopropylmethyldiethoxysilane were mixed with a magnetic stirrer for 24 hours at 50° C. The resulting homogenous mixture had a viscosity of 370 mPa·s (Brookfield RVDV-I+ viscometer, Spindle 4, speed 100 RPM) at 25° C.

6.0 g Lutensol® T08 was mixed into to 15.0 g of the resulting mixture described above for 20 s at 3000 rpm in a Hausschild dental mixer. An additional 1.1 g of water was added and mixing repeated under the same conditions. Further sequential additions of water took place with subsequent mixing in each instance until 26.2 g water had been added in total, yielding a micromeulsion with approx. 30% active content. which had a particle size of D(v, 0.1) nm=75.5, D(v, 0.5) nm=108.5 (Measured with a Nanotrac particle sizer in the volume mode).

Example 5

In a SpeedMixer™ (DAC 150 FVZ) was mixed 18 g of a hydroxyl terminated polydimethylsiloxane having a viscosity of 90 centiPoise (cP) (90 mPa·s), 5 g of a mixture consisting of 73% 3-(trimethoxysilyl)propyldimethyloctadecylammonium chloride, 15% chloropropyltrimethoxysilane and 12% dodecyl alcohol, and 2 g mineral oil (Hydroseal G 250H) until homogeneous. The homogeneous mixture had a viscosity of 80 cP (80 mPa·s). To this homogeneous mixture was added 0.3 g 1,1,3,3-tetramethylguanidine and 0.2g octanoic acid and again mixing took place until homogeneous. The resulting mixture was stored at 50° C. for 20 hours to allow polymerization, and was then cooled down to room temperature. The viscosity of the polymerized mixture was 2,534 cP (2,534 mPa·s).

To 19 g of the above polymerized mixture was added 2.34 g of undeceth-5 (Genapol® UD050) and 5.53 g undeceth-11 (Genapol® UD110), and the content was spun in a SpeedMixer™ at 3500 RPM for 22 sec. 3.0 g water was added, and the mixture was stirred by a spatula forming a clear to hazy mixture, and the mixture was then spun under the same condition. Two additional portions of water, 3.0 g each, were added, each time followed by spin under the same condition. The mixture became clear and highly viscous. An additional 21 g of water was added followed by spin under the same condition, arriving at a clear aqueous microemulsion with a slight bluish haze. The microemulsion had a mono-modal particle size distribution with a median particle diameter of 37.3 nanometers and 90% of the particles smaller than 57.0 nanometer, as measured using a Nanotrac™ (UPA150) particle sizer in the volume mode.

Comparative Example 1

The procedure of Example 1 Part C was repeated except that 12 grams of C12-15 alkylbenzoate was substituted in place of the product from Part B of Example 1. This resulted in an opaque white emulsion having a mono-modal particle size distribution centered around 371 nm.

Comparative Example 2

The procedure of Example 1 Part D was repeated except that 10 grams of C12-15 alkylbenzoate was substituted in place of the product from Part B of Example 1. This resulted in an opaque white emulsion having a mono-modal particle size distribution centered around 294 nm.

Comparative Example 3

The emulsification part of Example 5 was repeated except that 19 grams of mineral oil (Hydroseal® G 250H) was substituted in place of the polymerized siloxane mixture containing the mineral oil as the inert fluid in that example. This did not result in any emulsion as the oil and water remained separated after emulsification attempt.

These comparative examples illustrate that it is extremely difficult, if not impossible, to produce microemulsions from the majority, if not all, of these inert fluids on their own.

The invention claimed is:
1. A method of making an oil-in-water microemulsion containing (A) a polysiloxane and (B) a non-volatile inert fluid having viscosity of from 0.65 mPa·s to 10000 mPa·s at

25° C. and selected from a non-volatile inert siloxane fluid and a non-volatile inert organic fluid, where the average emulsion particle size is between 1 and 140 nanometers, said method comprising the steps of:
   a) preparing an oil phase comprising a polysiloxane containing mixture by the polymerisation of
      silane or siloxane containing monomers and/or oligomers in the presence of
      the non-volatile inert fluid (B),
      a suitable catalyst, and
      optionally an end-blocking agent;
   b) optionally quenching the polymerisation;
      wherein the non-volatile inert fluid (B) is substantially retained within the resulting polysiloxane containing mixture in an amount of from 5% to 70% w/w;
   c) optionally mixing one or more surfactants into the oil phase;
   d) adding water to the oil phase;
   e) applying agitation or shear to the polysiloxane containing mixture to arrive at an oil-in-water microemulsion; and
   f) optionally diluting the oil-in-water microemulsion by adding more water.

2. The method in accordance with claim 1, wherein the polysiloxane (A) is prepared via a polymerisation process selected from the group of polycondensation, chain extension, polyaddition, and ring opening.

3. The method in accordance with claim 1, wherein the polysiloxane (A) after polymerization contains less than 0.5% by weight of siloxanes of boiling point lower than 250° C.

4. The method in accordance with claim 1, wherein the one or more surfactants are present in the oil phase and wherein the catalyst is one of the one or more surfactants used for emulsification.

5. The method in accordance with claim 1, wherein the oil phase has a viscosity of from 100 mPa·s to 1000000 mPa·s at 25° C.

6. The method in accordance with claim 1, wherein the polysiloxane (A) comprises siloxy units having the formula

wherein
   each R is the same or different and is an alkyl group containing 1 to 8 carbon atoms, a substituted alkyl group containing 1 to 6 carbon atoms, or a phenyl group;
   $R^1$ is a hydroxy group, a hydrolysable group, or an unsaturated organic group;
   a is zero or 1; and
   b is an integer equal to a value of at least 200.

7. The method in accordance with claim 6, wherein the polysiloxane (A) comprises one or more substituted alkyl groups, each of which groups contain at least one polar group attached to silicon through a silicon-carbon bond or a silicon-oxygen-carbon bond.

8. The method in accordance with claim 6, wherein b is equal to a value of at least 1500.

9. The method in accordance with claim 6, wherein the polysiloxane (A) additionally comprises one or more $[RSiO_{3/2}]$ units and/or $[SiO_{4/2}]$ units.

10. An oil-in-water microemulsion obtained in accordance with the method of claim 1.

11. An oil-in-water microemulsion containing:
   (A) a polysiloxane; and
   (B) a non-volatile inert fluid;
wherein the average particle size of the emulsion is between 1 and 140 nanometers.

12. The oil-in-water microemulsion in accordance with claim 10, wherein the non-volatile inert fluid (B) is selected from the group of a trialkylsilyl terminated polydialkylsiloxane having a viscosity of from 0.65 mPa·s to 10000 mPa·s at 25° C.; a cyclic siloxane having from 2 to 20 silicon atoms; a polyisobutylene; an alkylbenzene, a mineral or white oil, an aliphatic or aromatic ester and ether; a glyceride; a fatty alcohol and a natural oil or a natural oil derivative.

13. The oil-in-water microemulsion according to claim 10, wherein the polysiloxane (A) contains one or more siloxane units having SiC-bonded groups containing basic nitrogen.

14. The oil-in-water microemulsion according to claim 10, wherein the polysiloxane (A) contains one or more siloxane units having SiC-bonded groups containing a quaternary ammonium group.

15. A cosmetic or personal care product comprising the oil-in-water microemulsion obtained in accordance with the method of claim 1.

16. The oil-in-water microemulsion in accordance with claim 11, wherein the non-volatile inert fluid (B) is selected from the group of a non-volatile trialkylsilyl terminated polydialkylsiloxane having a viscosity of from 0.65 mPa·s to 10,000 mPa·s at 25° C.; a cyclic siloxane having from 2 to 20 silicon atoms; a polyisobutylene; an alkylbenzene, a mineral or white oil, an aliphatic or aromatic ester or ether; a glyceride; a fatty alcohol and a natural oil or a natural oil derivative.

17. The oil-in-water microemulsion according to claim 11, wherein the polysiloxane (A) contains one or more siloxane units having SiC-bonded groups containing basic nitrogen.

18. The oil-in-water microemulsion according to claim 11, wherein the polysiloxane (A) contains one or more siloxane units having SiC-bonded groups containing a quaternary ammonium group.

19. A method of making an oil-in-water microemulsion containing (A) a polysiloxane and (B) a non-volatile inert fluid, where the average emulsion particle size is between 1 and 140 nanometers, said method comprising the steps of:
   a) preparing an oil phase comprising a polysiloxane containing mixture by the polymerisation of
      silane or siloxane containing monomers and/or oligomers in the presence of
      the non-volatile inert fluid (B) which is unreactive towards any other constituents, has a viscosity of from 0.65 mPa·s to 10000 mPa·s at 25° C., and is selected from an organopolysiloxane extender and/or plasticiser, an organic extender and/or plasticiser, and a cyclic siloxane comprising between 2 and 20 silicon atoms,
      a suitable catalyst, and
      optionally an end-blocking agent;
   b) optionally quenching the polymerisation;
      wherein the non-volatile inert fluid (B) is substantially retained within the resulting polysiloxane containing mixture in an amount of from 5% to 70% w/w;
   c) optionally mixing one or more surfactants into the oil phase;
   d) adding water to the oil phase;
   e) applying agitation or shear to the polysiloxane containing mixture to arrive at an oil-in-water microemulsion; and f) optionally diluting the oil-in-water microemulsion by adding more water.

20. The method in accordance with claim 19, wherein the non-volatile inert fluid (B) is selected from the group of a trialkylsilyl terminated polydialkylsiloxane; a cyclic siloxane having from 3 to 20 silicon atoms; a polyisobutylene; an alkylbenzene, a mineral or white oil, an aliphatic or aromatic ester, an aliphatic or aromatic ether; a glyceride; a fatty alcohol, a natural oil, and a natural oil derivative.

21. The method in accordance with claim 1, wherein the non-volatile inert fluid (B) is substantially retained within the resulting polysiloxane containing mixture in an amount of from 5% to 60% w/w.

22. The method in accordance with claim 21, wherein the non-volatile inert fluid (B) is substantially retained within the resulting polysiloxane containing mixture in an amount of from 5% to 50% w/w.

23. The method in accordance with claim 19, wherein the non-volatile inert fluid (B) is substantially retained within the resulting polysiloxane containing mixture in an amount of from 5% to 60% w/w.

24. The method in accordance with claim 23, wherein the non-volatile inert fluid (B) is substantially retained within the resulting polysiloxane containing mixture in an amount of from 5% to 50% w/w.

\* \* \* \* \*